United States Patent [19]

Richardson

[11] Patent Number: 5,038,761
[45] Date of Patent: Aug. 13, 1991

[54] THERAPEUTIC APPARATUS FOR PHYSICALLY IMPAIRED CHILDREN

[76] Inventor: Beverly J. Richardson, 17 W. 173 Oak La., Bensenville, Ill. 60106

[21] Appl. No.: 502,620

[22] Filed: Apr. 2, 1990

[51] Int. Cl.$^5$ ............................................. A61F 5/01
[52] U.S. Cl. ...................... 128/80 C; 2/24; 128/68; 297/423
[58] Field of Search ............ 128/68, 80 R, 80 A, 128/80 C, 80 F, 80 G, 882, ; 297/423; 5/443; 2/24

[56] References Cited

U.S. PATENT DOCUMENTS

| | | | |
|---|---|---|---|
| 1,251,040 | 12/1917 | Jenney et al. | 2/24 |
| 2,448,427 | 8/1948 | Gordon . | |
| 2,480,406 | 8/1949 | Forney . | |
| 2,484,494 | 10/1949 | Ferguson . | |
| 2,637,301 | 2/1953 | Emmett . | |
| 3,025,526 | 3/1962 | Ramon . | |
| 3,084,458 | 4/1963 | Ramon . | |
| 3,112,812 | 12/1963 | Ramon | 2/24 X |
| 3,258,779 | 7/1966 | Turner | 2/24 |
| 3,532,336 | 10/1970 | Baker . | |
| 3,863,978 | 2/1975 | Gillings, Jr. . | |
| 3,908,198 | 9/1975 | Brock . | |
| 4,377,309 | 3/1983 | Mengshoel . | |
| 4,589,699 | 5/1986 | Dungan | 297/423 |
| 4,599,748 | 7/1986 | Garcia | 2/22 |
| 4,772,071 | 9/1988 | Richards | 297/423 |

Primary Examiner—Robert A. Hafer
Assistant Examiner—Sam Rimell
Attorney, Agent, or Firm—Wood, Phillips, Mason, Recktenwald & VanSanten

[57] ABSTRACT

A therapeutic device for embracing each of the lower legs of a child having neurological, muscular and skeletal impairment generally caused by congenital disorders such as cerebral palsy, down syndrome, spina bifida and the like. The structure of the device promotes proper symmetrical alignment of the child's pelvis and lower extremities to program the child into more normal positioning and movement patterns of both the lower and upper body extremities. A single pair of the devices is adapted for children of varying ages and physical sizes.

22 Claims, 4 Drawing Sheets

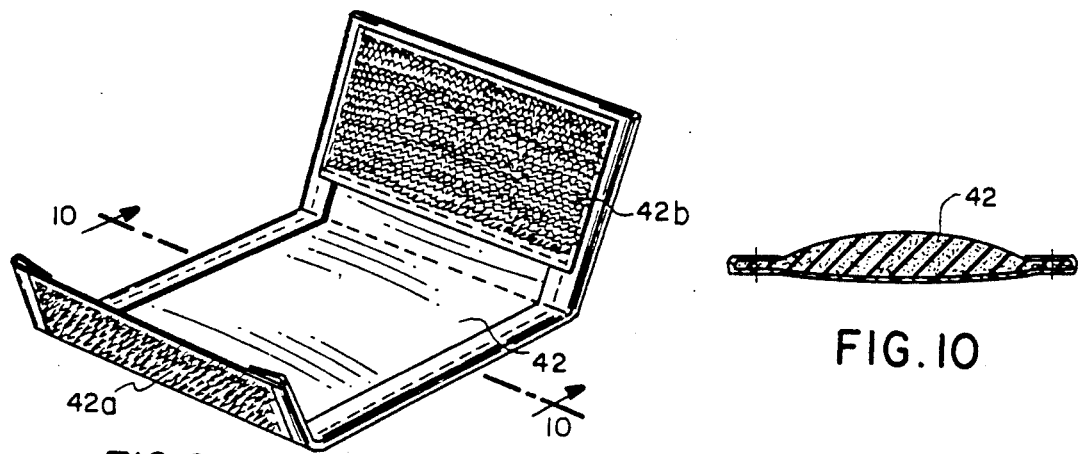
FIG. 9
FIG. 10
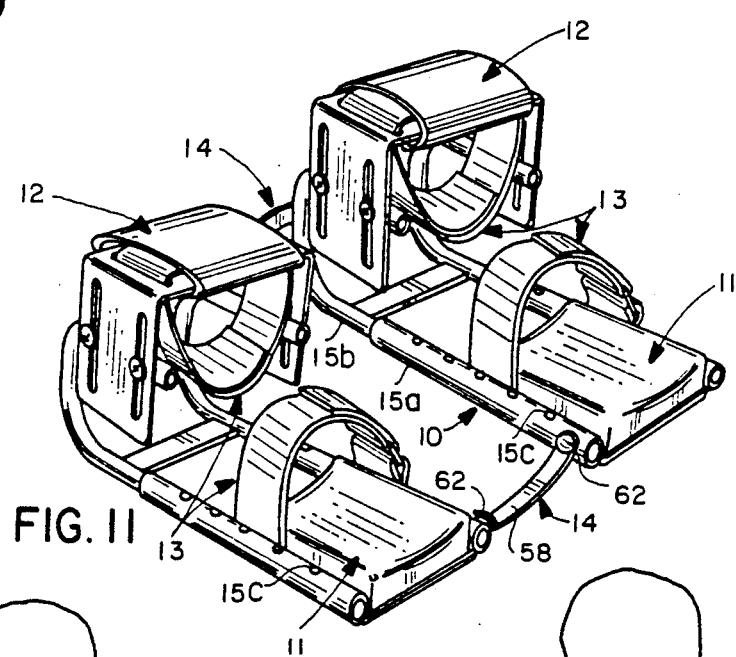
FIG. 11
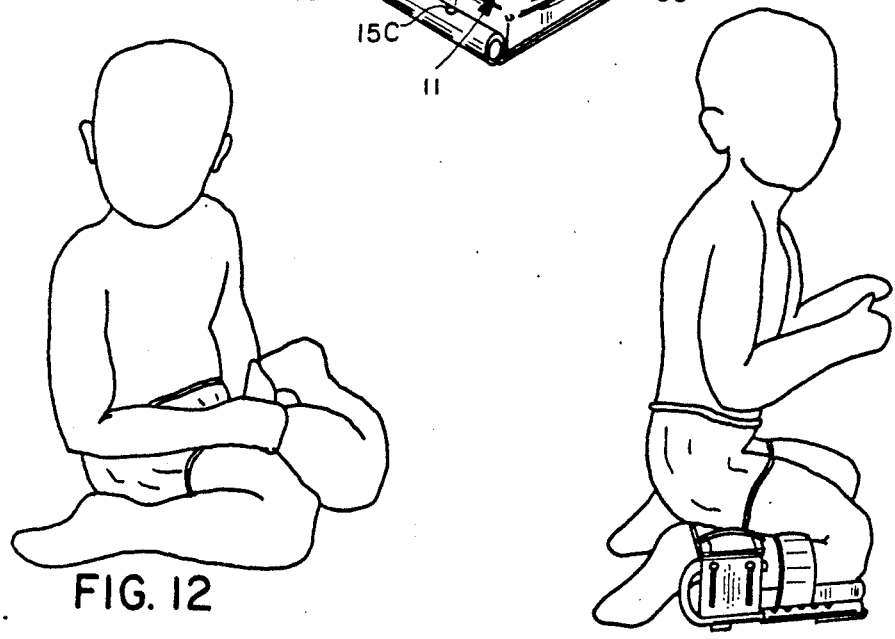
FIG. 12
FIG. 13

THERAPEUTIC APPARATUS FOR PHYSICALLY IMPAIRED CHILDREN

FIELD OF THE INVENTION

This invention relates to therapeutic apparatus for a physically impaired child, and more particularly to an apparatus for use by children who have neurological disorders resulting in impairment of their muscular-skeletal structures and of their bodily motor capabilities.

BACKGROUND OF THE INVENTION

The present invention provides a therapeutic aid for children suffering from muscular-motor afflictions generally congenital in nature. Typical of such congenital disorders are cerebral palsy, Down syndrome and spina bifida which may affect one or both sides of the body in varying degrees. Children afflicted with such diseases generally have impaired neurological capabilities and responses, weak muscle tone impairing normal physical bodily movements, mental retardation in some instances, and poor weight bearing patterns resulting in lack of stability and lack of normal symmetrical posture necessary for normal patterns of movement. Many of such children need ankle-foot-orthoses (AFO's) to correct muscular skeletal misalignments of the lower extremities including the foot, ankle and lower leg. Each afflicted child has a constant battle with the force of gravity because his muscular, motor and skeletal capabilities are deficient in controlling the center of gravity of his body in a normal manner.

When playing on the floor, the most common position assumed by children with the above disabilities is W-sitting (illustrated diagrammatically in FIG. 12). As the term suggests, the legs and lower extremities of the body assume a W configuration. The disabled child sits back between the knees with lower legs outstretched in an attempt to stabilize the pelvis and to impart balance to the trunk and upper torso; but such a position prevents normal and proper use of the upper extremities for the activities presented by a play program.

Additionally, this position tends to immobilize the child and prevents enjoyment of play activities; it frequently leads to further hip, knee, ankle and foot deformities; and it positions the child's back in a stooped, misaligned posture with the neck hyperextended and the shoulders rounded forwardly. Heretofore, there has not been any equipment, aid or device to assist the pediatric physical therapist in correcting and helping with this persistent problem so that the child can independently partake in the planned program of play without constant attention of a physical therapist or other attendant.

SUMMARY OF THE INVENTION

The device of the present invention resolves the above W-sitting problems by providing a stable base and seat which force the child to heel sit during the floor playing program. The device enhances control of lower extremity rotation; it keeps the pelvis and legs aligned to provide a normally extended foot position and it provides for symmetrical body orientation resulting in improved postural control, more normalized movement patterns and better control of the child's center of gravity. In effect, each pair of devices of the present invention provides an extra pair of hands for the attending physical therapist because constant attention need not be devoted to a single child utilizing the devices.

Furthermore, by providing and controlling proper symmetrical body alignment, the device of the invention enables the afflicted child to partake to a greater extent in normal play activities by knee standing, creeping and ultimately walking with the inventive equipment aid in position on the lower legs.

The primary object of the present invention is to provide a therapeutic device for a physically impaired child which will enhance physical movements and mobility during a floor play program while maintaining proper alignment of the muscular skeletal structure of the child.

Another object of the invention is to increase muscular skeletal strength of such a child and to increase selfreliance so that the child may partake in group floor play independent of constant attention of a physical therapist or other supervising attendants.

A further object is to provide a therapeutic device which will provide such a child with lower extremity alignment and stability which will encourage normal ankle and foot positioning.

Another object of the present invention is to provide a therapeutic aid for each lower leg of such a child, the aid having stable frame and seat assemblies, each of which is adjustable to accommodate children of varying heights.

Still another object is to provide a therapeutic aid for each lower leg of such a child having adjustable embracing means associated with the frame assembly for holding each lower leg in longitudinal alignment with the frame assembly from the ankle to the knee.

Yet another object of the invention is to provide a pair of therapeutic devices, one for each leg of a physically impaired child, the devices being provided with flexible restraining means extending between adjacent portions of the devices to prevent excessive lateral movement of the devices away from each other, the restraining means being adjustable to predetermine the extent of lateral movement permitted between the devices.

To accomplish the above objects and other objects as pointed out hereinafter, each device of the pair of therapeutic devices includes a frame assembly having an upper member and an elongated lower member for supporting the frame assembly on an underlying surface, the frame assembly being further provided with laterally offset upright means supporting the upper member in spaced relation above the rear portion of the lower member so that the lower leg of a child can be positioned longitudinally of the frame assembly between the upper member and rear portion of the lower member of the frame. Each device is also provided with a seat on the upper member for the posterior of the child, and with a concave knee pad on the front portion of the lower member of the frame to receive the knee of the child in kneeling position. Flexible embracing means are attached fore and aft of the frame for encircling the lower leg of the child to hold the lower leg to the frame assembly from the ankle to the knee so that the lower leg and the frame assembly move together as a unit to constrain the muscular-skeletal body structure of the child in normal symmetrical alignment.

BRIEF DESCRIPTION OF THE DRAWINGS

The device is illustrated in a preferred embodiment in the accompanying drawings in which:

FIG. 9 is a perspective view of the padded seat together with the extensions mounting the hook and eye means for holding the seat in position about the central portion of the inverted saddle;

FIG. 10 is a sectional view taken as indicated on line 10—10 of FIG. 9;

FIG. 11 is a perspective view of a pair of the devices disposed in normal operating position;

FIG. 12 is a perspective view of a physically impaired child in a "W-Sitting" position which the present invention is designed to prevent;

FIG. 13 is a perspective view of a child having the device of the invention on each lower leg, the device positioning the child in the proper knee sitting position with the child's body in proper symmetrical alignment;

DESCRIPTION OF THE PREFERRED EMBODIMENT

Figure 1:
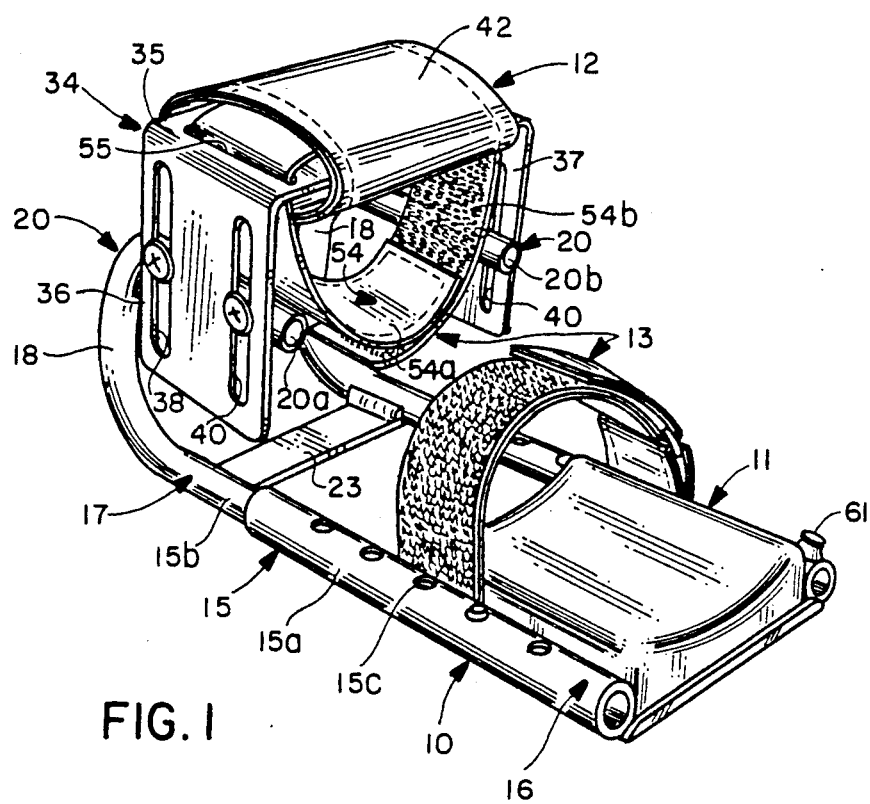
FIG. 1 is a perspective view of one of the therapeutic devices with the forward and rearward straps in secured position.

The device of the present invention is intended to be used in pairs, that is, one device on each of the lower legs of the child. Each device of the pair of devices is substantially identical in structure and in function; therefore, only a description of one of the devices is needed to understand the operation and utility of the invention. Each device includes a frame assembly, generally designated 10, a knee receiving assembly, generally designated 11; a seat assembly, generally designated 12; lower leg embracing means, generally designated 13; and flexible restraining means, generally designated 14, extending between the pair of devices to limit lateral movement between the devices when in use.

Figure 15:
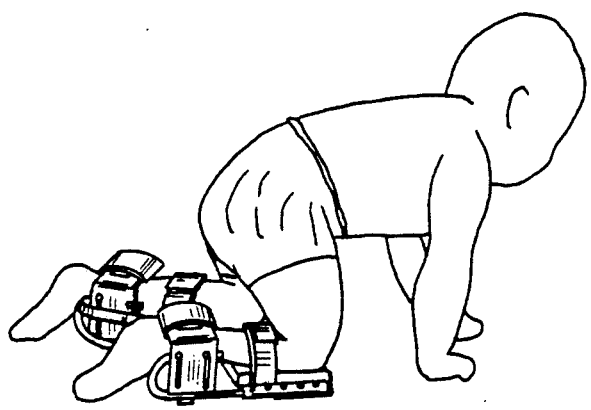
FIG. 15 is a perspective view showing a pair of the devices mounted on each of the lower legs of a child with the child in a proper creeping or crawling position.
Figure 16:
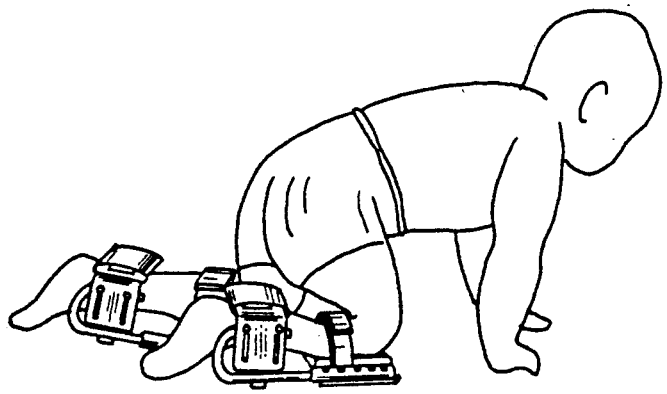
FIG. 16 is a view similar to FIG. 15 in which the restraining straps between the devices are removed to permit greater freedom of leg movement.
Figure 17:
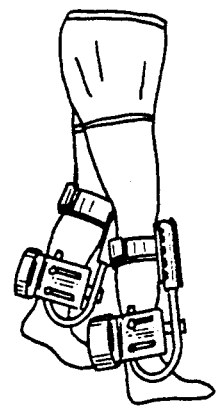
FIG. 17 is a fragmentary perspective view showing the legs of the child with the devices mounted thereon when the child is in a walking position with restraining straps removed.

The frame or frame assembly 10 is purposefully made light in weight so that even a severely physically impaired child can move with the device applied, for example when in a crawling position, as in FIGS. 15 and 16. Additionally, the portions of the frame in contact with an underlying surface are formed of material having a low coefficient of friction in relation to s id surface which is normally of wood as in the usual gymnasium floor. As will be further seen, certain portions of the frame are identically formed which result in less manufacturing costs and increased manufacturing conveniences.

Figure 4:
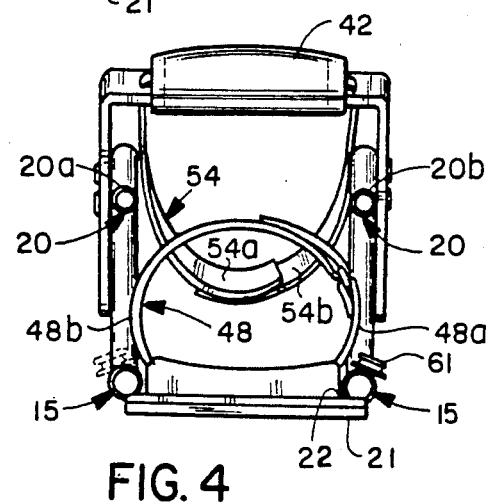
FIG. 4 is a front elevational view of the device taken from the right of FIGS. 1 and 2.

To this end, the frame 10 is preferably provided with a pair of similar aluminum tubular rails or runners 15 spaced laterally of the frame 10 to provide a stable base for supporting the device on an underlying surface. Each tubular rail 15 preferably extends in a straight line from front to rear of the frame 10 to afford a front portion 16 and a rear portion 17. At the rear portion 17 of the frame 10 upright means 18 is provided which is offset laterally of the longitudinal axis of the frame 10. As herein shown, each tubular aluminum rail is arcuately bent upwardly to form both said upright means 18 and an upper member 20 for supporting the seat assembly 12 spaced above the rear portion 17 of the frame 10. The upper member 20 includes tubular portions 20a and 20b as best shown in FIGS. 1 and 4.

Figure 7:
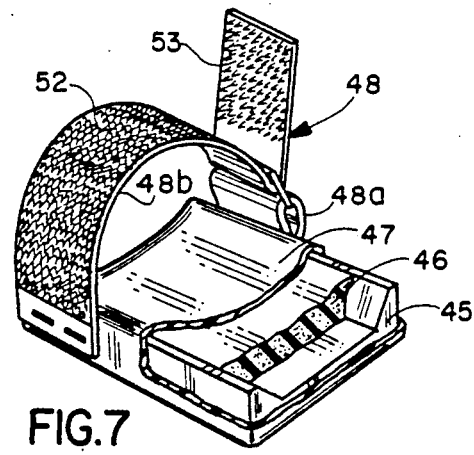
FIG. 7 is a broken fragmentary perspective view of the knee receiving assembly, the rails of the frame assembly being removed for clarity of illustration.
Figure 8:
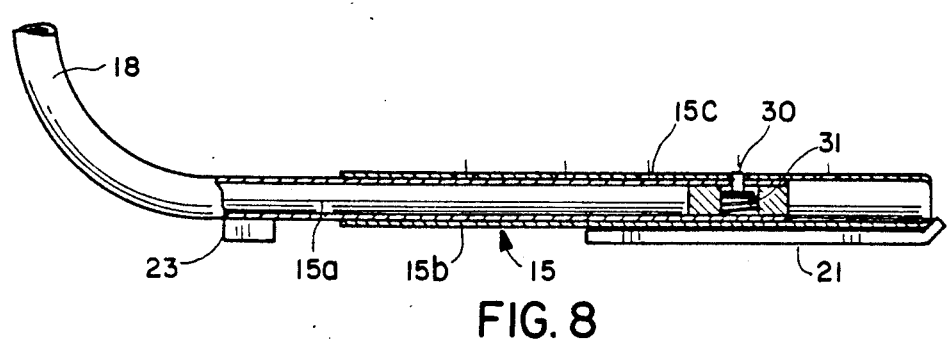
FIG. 8 is a fragmentary side elevational view partly in section of each of the rails or runners of the frame assembly showing the telescoping elements forming each rail and the latch means for holding the telescoping elements of each rail in one of a number of preselected positions.
Figure 14:
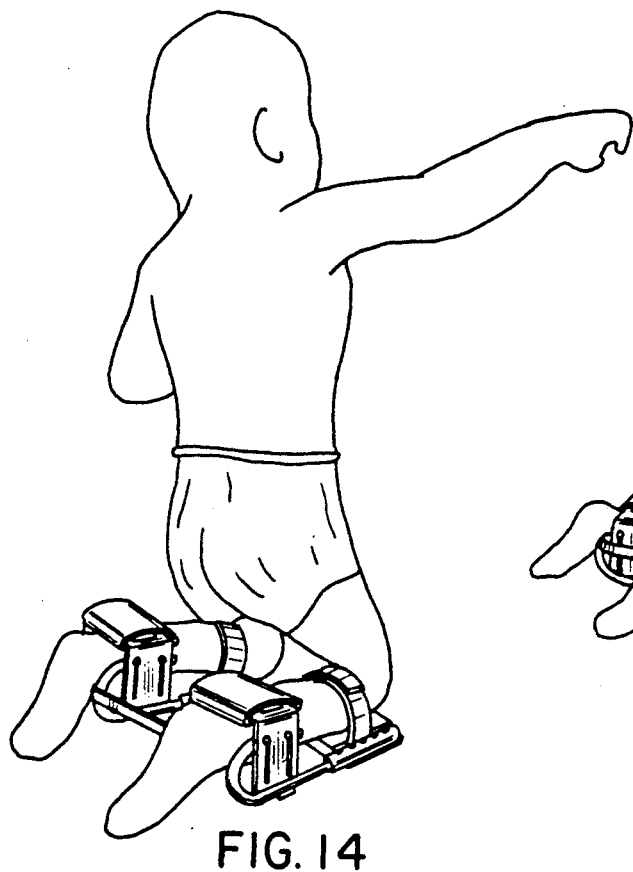
FIG. 14 is a view similar to FIG. 13 but showing the child in a knee standing position with the body in proper symmetrical alignment.

Each of the rails is rigidly held in laterally spaced relation by interconnecting means fore and aft of the frame 10, which interconnecting means preferably contacts the underlying surface and provides support for the rails of the frame. The interconnecting means preferably includes a flat rectangular member 21 at the front of the frame extending between and secured to each of the rails in a convenient manner such as by a weld 22; similarly, a narrow rectangular member 23 extends transversely between the rails at the rear portion 17 of the frame and is likewise secured to each of the rails in a convenient manner as by weld 24. As best shown in FIGS. 4, 7 and 8, rail interconnecting member 21 also provides underlying support for knee assembly 11, and has a forward marginal edge portion 25 (FIG. 8) which is gently angled upwardly to prevent the device from engaging and catching on an exposed sharp corner of an underlying surface when the child is creeping or crawling.

Figure 2:
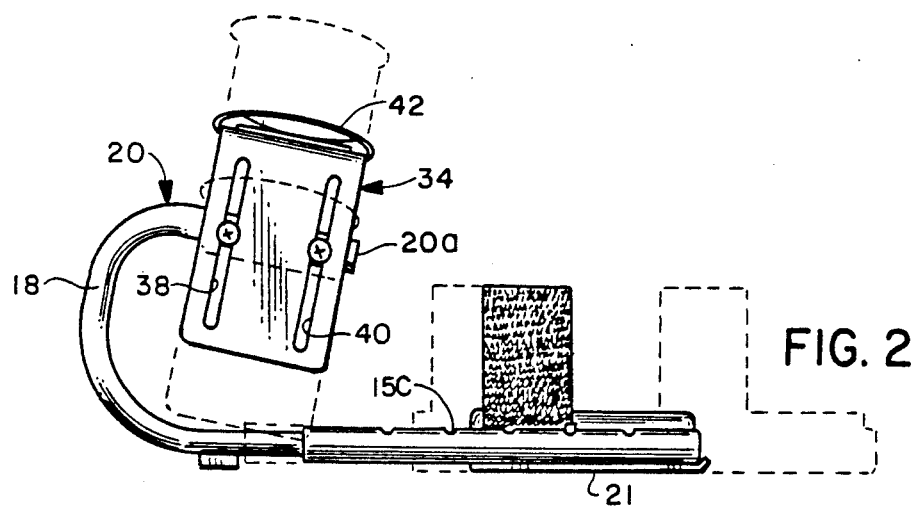
FIG. 2 is a side elevational view of the device of FIG. 1 illustrating in dotted outline the vertical adjustability of the seat assembly and the longitudinal adjustability of the knee assembly.

The invention is designed to accommodate various lower leg lengths of physically impaired children of varying ages and of varying heights. To this end, each of the rails 15 preferably includes telescoping elements 15a and 15b. As shown herein, the front tubular element 15a is of a size to telescopingly receive the rear tubular element 15b in a close fit throughout so as to maintain stability in the respective telescoping elements and in the interconnecting means 21,23 which is in contact with the underlying floor or other supporting surface. As best seen in FIGS. 1, 2, 5 and 8, each front telescoping element 15a has a number of similar spaced apertures 15c. The apertures 15c are each of a size to receive an upwardly urged plunger type latch 30 mounted securely in the forward end of rear tubular element 15b, each latch 30 being normally urged upwardly by a spring 31. The latch and spring in the forward end of each rear tubular element 15b is held against longitudinal displacement by adjacent fore and aft stops 32 and 33. Thus by simultaneously depressing each of the latches 30, the telescoping elements 15b may be moved either forwardly or rearwardly of latching engagement with similarly positioned apertures 15c in front tubular elements 15a to lengthen or shorten the rails or runners 15, as shown in FIG. 2. In this manner, the frame may be lengthened or shortened as desired to accommodate varying lengths of the lower leg portions of children using the device. Since the knee receiving assembly 11 is mounted on the front portion 16 of the frame 10, relative movement between the telescoping elements 15a and 15b also varies the position of knee assembly 11 so that knee assembly 11 may be properly positioned by the pediatric physical therapist for the particular child.

Figure 5:
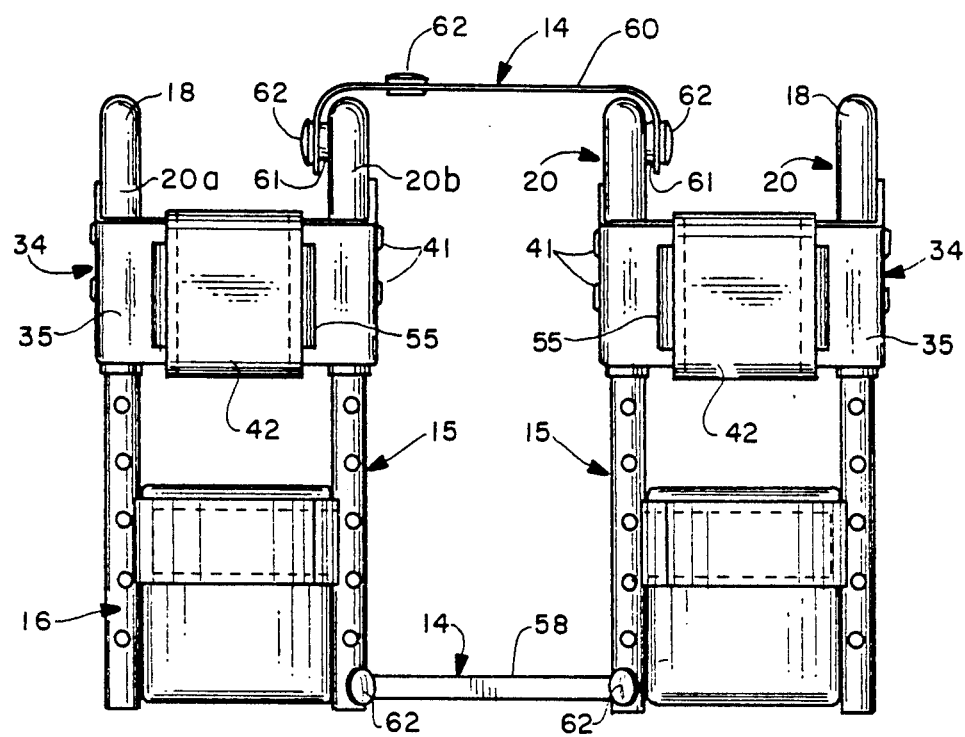
FIG. 5 is a top plan view of the two therapeutic devices connected by the restraining means and disposed in normal operating position.

Means are also provided for adjusting the seat assembly 12 to accommodate children of varying ages and sizes. As best shown in FIGS. 1, 2 and 5, the seat assembly includes an inverted U-shaped saddle 34 of a size to laterally straddle the upper member 20. The saddle 34 includes a platform 35 extending laterally between tubular portions 20a and 20b and a pair of similar leg portions 36,37 extending downwardly from opposite ends of platform 35 closely adjacent to opposite sides of the upper member 20.

Figure 6:
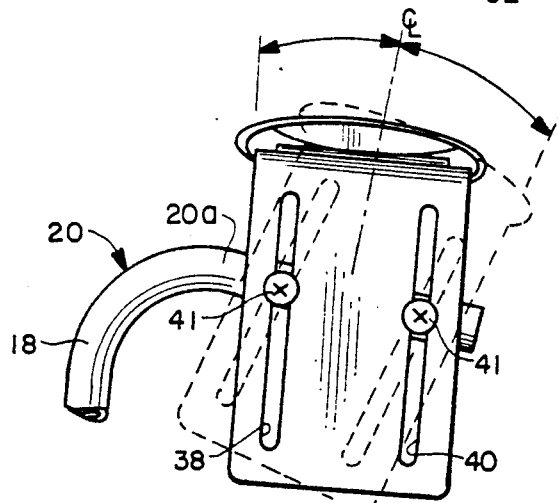
FIG. 6 is a fragmentary side elevational view of the seat assembly illustrating its tiltability in dotted outline.

The platform 35 reinforces and adds stability to the upper member 20; and in addition, the platform 35 is adjustable in height and in angular orientation fore and aft to accommodate the physical requirements of the particular child. For these purposes each leg portion is provided with a pair of spaced slots 38,40 each for accommodating Phillips head screws 41 which are received in threaded openings in the lateral surfaces of each tubular portion 20a,20b of upper member 20. By utilizing a Phillips screwdriver, the screws 41 may be loosened (and subsequently retightened) so that the saddle 34 and its leg portions 36,37 may be adjustably moved upwardly or downwardly to vary the vertical height of the platform 35, as shown in FIG. 2. If desired, the angle of the platform 35 may also be slightly angularly varied toward or away from the horizontal as shown in slightly exaggerated fashion in FIG. 6. Such fore and aft rotative motion is permitted because of the normal clearance tolerances between the shanks of screws 41 and the sides of spaced slots 38,40. When the screws 41 are tightened, the upper member 20 is reinforced by platform 35 and leg portions 36,37.

The seat assembly 12 preferably includes a replaceable padded member 42 which encircles the platform 35 as shown in FIG. 1. The padded member 42 is best shown in FIGS. 9 and 10, and it includes flexible end portions 42a,42b provided with conventional hook and eye portions sold under the trademark Velcro. The padded member 42 is positioned on top of platform 35, and end portions 42a,42b are folded beneath the platform 35 to releasably engage the hook and eye portions and upwardly expose the padded member 42.

The knee receiving assembly 11 is best shown in FIG. 7. A longitudinally extending troughlike member 45 is mounted on the rectangular member 21 between the rails 15 of the front portion 16 and is shaped to receive a resilient rubber or plastic piece 46 which has a concave upper surface for engaging the curvature of the knee. A plastic or similar covering 47 encircles the knee receiving assembly which is held to the rectangular member 21 by conventional securing means such as machine screws (not shown) passing from the underside of member 21 into threaded openings of member 45.

The embracing means 13 is provided for encircling the lower leg of the child to hold the lower leg to the frame 10 from the ankle to the knee so that the lower leg and the frame have little or no relative movement therebetween, that is, the lower leg and frame move together generally in a unitary fashion. As herein shown, embracing means are positioned to encircle the malleoli (ankle bones) and the upper ends of the tibia and fibula of the lower leg. To this end, embracing means 13 includes a front adjustable strap 48 for the purpose of encircling the upper portion of the calf of a child's leg just below the knee. The strap consists of a first strap portion 48a and a second strap portion 48b. The strap portion 48a is anchored in a conventional manner at one end between rail 20 and knee assembly 11 (FIG. 4) and is provided with a D-ring on its free end. The second strap portion 48b has one end similarly anchored between rail 20 and knee assembly 11 (best shown in FIGS. 4 and 7) and is provided on its upper surface with spaced hook and eye elements 52,53 as previously described in relation to padded member 42. Strap portion 48b is of a size to pass through the D-ring (FIG. 7) and then is pulled back upon itself to engage hook and eye elements 52,53 (as shown in FIG. 4). This structure enables strap portion 51 to be adjustable so as to firmly, yet comfortably, encircle the upper calf of a child regardless of calf size.

Figure 3:
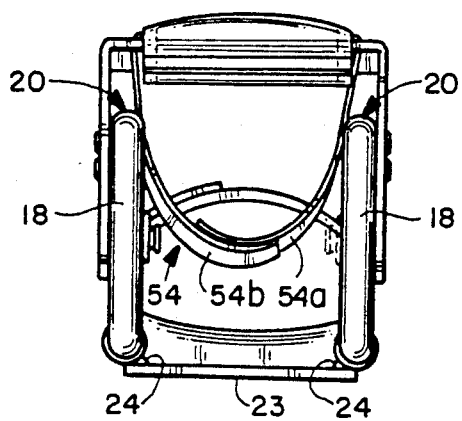
FIG. 3 is a rear elevational view of the device taken from the left of FIG. 2.

The embracing means 13 is also preferably includes a rear adjustable strap 54, as best shown in FIGS. 1 and 3. Rear strap 54 is threaded through each of two longitudinally extending slots 55 located at opposite ends of the platform 35 so that the central portion of rear strap 54 extends across the top of platform 35 and beneath padded member 42. Each free end of rear strap 54 is provided with cooperating hook and eye elements 54a,54b, as previously described, which are detachably engagable to form a depending sling for supporting the ankle of the child. Adjustability of rear strap 54 permits firm and comfortable engagement with the ankle, and also supports the ankle and foot in a normal extended position, which position is aided by the lower body alignment provided by the frame, knee and seat assemblies. Further, ankle-foot orthoses (AFO's) used by some children with severe physical impairment need not be removed when utilizing the present invention because adequate spacing for the braces (or casts) is provided by the adjustable seat assembly 12 and the adjustable strap 54. Professional judgment of an attending physical therapist should be obtained to determine the advisability of keeping AFO's or removable casts in place on the lower leg extremities while the child is playing on the floor.

Restraining means 14 is provided to limit lateral movement of the devices away from each other, and is needed generally with children who suffer more severe muscular and structural physical impairment, that is, children who suffer extreme abduction problems and are severely lacking in physical control of their lower extremities.

The restraining means (best shown in FIGS. 5 and 11) preferably comprises elongated flexible elastic bands 58,60 extending between the devices at the front and rear respectively of each of the frames 10 to resiliently limit outward movement of the devices. Preferably snap fasteners are provided to detachably secure elastic bands 58,60 to the frame 10. As herein shown, the male fastener portions 61 are secured fore and aft of the frame each to accommodate or receive one of the female fastener portions 62 secured to bands 58,60. Preferably, additional portions 62 are secured to each of the bands 58,60 so that the maximum distance fore and aft between adjacent frames 10 can be varied as desired to accommodate a particular child. While the bands are preferably elastic, it is clear that a non-extensible flexible band may also be utilized to accomplish the function of the restraining means 14. As the more severely impaired child is programmed over a period of time into more normal movement and positioning patterns, the use of the restraining means ma be gradually decreased and ultimately eliminated provided that the child's muscular and skeletal control has advanced sufficiently.

To place the structure of the invention upon a child, the knee assembly 11 is adjusted longitudinally to correspond to the lower leg length from the ankle to the knee, and the seat assembly 12 is adjusted to a comfortable sitting position for the child. The child is then placed in the lap of the physical therapist or parent, and the device is inverted from the position shown in FIG. 1 with front and rear straps 48,54 of the embracing means detached and opened. The device is then moved to position the knee assembly 11 precisely over the child's knee and to position the seat assembly 12 under the child's ankle so that the child's foot extends outwardly between the tubular upright means 18. The front strap 48 is then secured about the upper calf muscle just below the knee, and the rear strap 54 is secured about the ankle. A second device is then similarly mounted on the other leg of the child, after which the child is lowered to a kneeling position with the frame 10 engaging the underlying supporting surface.

It should be understood that the foregoing detailed description was made for purposes of demonstrating the inventive structure and its operation, with no unnecessary limitations to be understood therefrom.

I claim:

1. A pair of therapeutic devices one for each lower leg of a physically impaired child to support the muscular-skeletal body structure of the child in proper symmetrical alignment in sitting position and in kneeling position, each of said devices comprising:

a frame having an upper member and an elongated lower member provided with a front portion and a rear portion for supporting the frame uprightly upon an underlying surface, the upper member being positioned above said rear portion, the frame being provided with upright means extending between the lower member and the upper member to maintain said members in spaced relation, the upright means being offset laterally of the longitudinal axis of the frame so that the lower leg of the child extends longitudinally of the frame with the ankle of the child positioned between said upper member and said rear portion of the lower member of the frame;

a seat mounted on the upper member of the frame to accommodate the posterior of the child in sitting position;

a knee pad mounted on the front portion of the lower member of the frame to receive the knee of the child in kneeling position; and flexible embracing means attached to the frame, said embracing means including a strap positioned forwardly of the frame to encircle the upper calf of the lower leg of the child below the knee, and a suspended sling positioned rearwardly of the frame and depending from the frame upper portion to cradle and support the ankle of the child in spaced relation from the underlying surface, the embracing means retaining the lower leg and frame together for movement as a unit whereby when the devices are positioned on each lower leg of the child and the child is in sitting position on each of said seats with a knee resting on each of said knee pads, the muscular-skeletal body structure of the child is constrained to assume normal symmetrical alignment.

2. A pair of therapeutic devices as specified in claim 1, in which the suspended sling of each device is adjustable to vary the distance in which the ankle of the child is supported with respect to the underlying surface.

3. A pair of therapeutic devices as specified in claim 1, in which each device includes a platform adjustably secured to the upper member for tilting movement forwardly and rearwardly of the frame, said platform having a laterally extending upper surface on which the seat is mounted for selected tilting movement with the platform.

4. A pair of therapeutic devices as specified in claim 1, in which each device has a platform adjustably secured to the upper member for movement upwardly and downwardly of the frame, said platform having a laterally extending upper surface on which the seat is mounted for selected movement upwardly and downwardly with the platform.

5. A pair of therapeutic devices one for each leg of a physically impaired child to support the muscular-skeletal body structure of the child in proper alignment in sitting position and in kneeling position, each of said devices comprising:

a frame having an upper member and an elongated lower member provided with a front portion and a rear portion for supporting the frame uprightly upon an underlying surface, the upper member being positioned above said rear portion the lower member having a pair of laterally spaced, longitudinally extending rails;

laterally extending interconnecting means for holding the rails in laterally spaced relation;

upright means offset laterally of the longitudinal axis of the frame and extending between the lower member and the upper member to maintain said members in spaced relation so that the lower leg of the child can be positioned longitudinally between the rails with the ankle positioned beneath the upper member of the frame;

a seat mounted on the upper member to accommodate the posterior of the child in sitting position;

a knee pad mounted on the front portion of the lower member of the frame to receive the knee of the child in kneeling position; and flexible embracing means attached fore and aft of the frame for encircling the lower leg of the child to hold the lower leg to the frame from the ankle to the knee so that the lower leg and the frame move together as a unit, whereby, when the devices are positioned on each lower leg of the child and the child is in sitting position on each of said seats with a knee resting on each of said knee pads, the muscular-skeletal body structure of the child is constrained to assume normal symmetrical alignment.

6. A pair of therapeutic devices as specified in claim 5 in which each of the elongated rails of each of said devices has a forwardly extending element and a rearwardly extending element which overlap, the elements being disposed for longitudinal sliding movement with respect to each other so as to vary the length of the lower member of the frame to accommodate children having different lengths of lower legs.

7. A pair of therapeutic devices as specified in claim 6, in which latch means are provided operative between the forwardly and rearwardly extending elements of each of said rails to hold the elements in a preselected position of adjustment.

8. A pair of therapeutic devices as specified in claim 7, in which at least one of the elements of each of said rails is tubular so as to telescopingly receive the other of the elements, and latch means are provided operative between the elements of each of said rails to restrain said sliding movement and to hold the elements of each rail in a preselected position of adjustment.

9. A pair of therapeutic devices as specified in claim 8, in which a platform is adjustably secured to the upper member of each frame for tilting movement forwardly and rearwardly of the frame, said platform having a laterally extending upper surface on which the seat of each device is mounted for selected tilting movement with the platform.

10. A pair of therapeutic devices as specified in claim 9, in which a platform is adjustably secured to the upper member of each frame for movement upwardly and downwardly of the frame, said platform having a laterally extending upper surface on which the seat of each device is mounted for selected movement upwardly and downwardly with the platform.

11. A pair of therapeutic devices as specified in claim 10, in which the upper member of the frame of each device has a second pair of spaced rails, and a platform is provided having a laterally extending upper surface bridging the space between said second pair of rails, the seat resting upon the upper surface of said platform and having detachable portions encircling said platform so that the seat may be removed and replaced.

12. A pair of therapeutic devices as specified in claim 11, in which the embracing means of each device includes a suspended sling positioned rearwardly of the frame and depending from the frame upper portion to cradle and support the ankle of the child in spaced relation from the underlying surface.

13. A pair of therapeutic devices as specified in claim 12, in which the embracing means of each device includes a suspended sling positioned rearwardly of the frame and depending from the frame upper portion to cradle and support the ankle of the child, said sling being adjustable to vary the distance in which the ankle of the child is supported with respect to the underlying surface.

14. A pair of therapeutic devices one for each lower leg of a physically impaired child to support the muscular-skeletal body structure of the child in proper symmetrical alignment in sitting position and in kneeling position, each of said devices comprising:
a frame having an upper member and an elongated lower member provided with a front portion and a rear portion for supporting the frame uprightly upon an underlying surface, the upper member being positioned above said rear portion, the frame being provided with upright means extending between the lower member and the upper member to maintain said members in spaced relation, the upright means being offset laterally of the longitudinal axis of the frame so that the lower leg of the child extends longitudinally of the frame with the ankle of the child positioned between said upper member and said rear portion of the lower member of the frame;
a seat mounted on the upper member of the frame to accommodate the posterior of the child in sitting position;
a knee pad mounted on the front portion of the lower member of the frame to receive the knee of the child in kneeling position;
restraining means attached to and extending between each of the devices to limit lateral movement of the devices away from each other; and
flexible embracing means attached fore and aft to the frame for encircling the lower leg of the child to hold the lower leg to the frame from the ankle to the knee so that the lower leg and frame move together as a unit whereby when the devices are positioned on each lower leg of the child and the child is in sitting position on each of said seats with a knee resting on each of said knee pads, the muscular-skeletal body structure of the child is constrained to assume normal symmetrical alignment 15. A pair of therapeutic devices as specified in claim 14, in which said restraining means includes a first flexible elastic ribbon attached to and extending between the forward portions of each frame lower member and a second flexible elastic ribbon attached to and extending between the rear portions of each frame lower member.

16. A pair of therapeutic devices as specified in claim 15, in which the restraining means includes a first flexible elastic ribbon attached to and extending between the forward portions of each frame lower member and a second flexible elastic ribbon attached to and extending between the rear portions of each said frame lower member, and releasable means are provided on each of the ribbons for detachably securing the ribbons to the forward and rear portions of each frame.

17. A pair of therapeutic devices one for each leg of a physically impaired child to support the muscular-skeletal body structure of the child in proper alignment in sitting position and in kneeling position, each of said devices comprising:
a frame having an upper member and an elongated lower member provided with a front portion and a rear portion for supporting the frame uprightly upon an underlying surface, the upper member being positioned above said rear portion, the lower member having a pair of laterally spaced, longitudinally extending rails;
laterally extending interconnecting means for holding the rails in laterally spaced relation;
upright means offset laterally of the longitudinal axis of the frame and extending between the lower member and the upper member to maintain said members in spaced relation so that the lower leg of the child can be positioned longitudinally between the rails with the ankle positioned beneath the upper member of the frame;
a seat mounted on the upper member to accommodate the posterior of the child in sitting position;
a knee pad mounted on the front portion of the lower member of the frame to receive the knee of the child in kneeling position;
flexible restraining means attached to and extending between each of the devices to limit lateral movement of the devices away from each other; and
flexible embracing means attached fore and aft of the frame for encircling the lower leg of the child to hold the lower leg to the frame from the ankle to the knee so that the lower leg and the frame move together as a unit, whereby, when the devices are positioned on each lower leg of the child and the child is in sitting position on each of said seats with a knee resting on each of said knee pads, the muscular-skeletal body structure of the child is constrained to assume normal symmetrical alignment.

18. A pair of therapeutic devices as specified in claim 17 in which flexible restraining means are provided attached to and extending between each of the devices, said restraining means being adjustable to vary the limit of lateral movement between the devices.

19. A pair of therapeutic devices as specified in claim 18, in which the flexible restraining means are adjustable to vary the limit of lateral movement between the devices.

20. A pair of therapeutic devices as specified in claim 19, in which each of the strap and suspended sling of the embracing means is adjustable to accommodate ankle-foot orthoses on the lower legs of the child.

21. A pair of therapeutic devices as specified in claim 20, in which the embracing means of each device includes a strap positioned forwardly of the frame to encircle the upper calf of the lower leg of the child below the knee, and a suspended sling positioned rearwardly of the frame and depending from the frame upper portion to cradle and support the ankle of the child in spaced relation from the underlying surface.

22. A pair of therapeutic devices as specified in claim 21, in which each of the strap and suspended sling of the embracing means is adjustable to accommodate ankle-foot orthoses on the lower legs of the child.

* * * * *